US00PP23745P3

(12) United States Plant Patent
Ackerman et al.

(10) Patent No.: US PP23,745 P3
(45) Date of Patent: Jul. 16, 2013

(54) STRAWBERRY PLANT NAMED 'MERIT'

(50) Latin Name: *Fragaria ananassa*
Varietal Denomination: MERIT

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 363 days.

(21) Appl. No.: 12/926,805

(22) Filed: Dec. 10, 2010

(65) Prior Publication Data

US 2012/0151646 P1 Jun. 14, 2012

(51) Int. Cl.
*A01H 5/00* (2006.01)

(52) U.S. Cl.
USPC ..... Plt./209

(58) Field of Classification Search
USPC ..... Plt./209
See application file for complete search history.

(56) References Cited

PUBLICATIONS

Printout of application information from Community Plant Variety Office (CPVO) website for corresponding CPVO application No. 2011/0145 filed Jan. 21, 2011 (1 page). (http://www.cpvoextranet.cpvo.europa.eu).

*Primary Examiner* — Annette Para
(74) *Attorney, Agent, or Firm* — Foley & Lardner LLP

(57) ABSTRACT

This invention relates to a new and distinct variety of strawberry plant named 'MERIT'. This new strawberry plant named 'MERIT' is primarily adapted to the growing conditions of the central coast of California, and is primarily characterized by its small fruit size; orange red to red fruit color; uniformly shaped conical berries; and small sized plant.

5 Drawing Sheets

Latin name of the genus and species of the plant claimed: *Fragaria ananassa.*

Variety denomination: 'MERIT'.

BACKGROUND OF THE INVENTION

The present invention relates to a new and distinct strawberry variety named 'MERIT'. This new variety is a result of a controlled cross made in 2001 in an ongoing breeding program between strawberry variety designated 'PS-2880' (patented, U.S. Plant Pat. No. 15,597) and strawberry variety designated 'PS-4630' (a non-patented selection). Due to the combining of the reciprocal seed lots it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, California in the fall of 2003. After its selection, the new variety was asexually propagated by stolons in both San Joaquin County, California and Siskiyou County, California. The new variety was extensively tested over the next several years in fruiting fields in Ventura County, California. This propagation has demonstrated that the combination of traits disclosed herein as characterizing the new variety are fixed and remain true to type through successive generations of asexual reproduction.

BRIEF SUMMARY OF THE INVENTION

'MERIT' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'MERIT', which in combination distinguish this strawberry plant as a new and distinct variety:

1. Small fruit size;
2. Orange-red to red fruit color;
3. Uniformly shaped, conical berries;
4. Small sized plant;
5. Fruiting trusses that are visible above the foliage; and
6. Relatively short fruiting trusses The strawberry varieties that are believed to be most closely related to the new strawberry variety 'MERIT' are the strawberry variety 'VALOR' (patented, U.S. Plant Pat. No. 20,394) and the strawberry variety 'PREMIER' (patented, U.S. Plant Pat. No. 20,309). In side-by-side comparisons to the similar strawberry varieties 'VALOR' and 'PREMIER', the new strawberry variety 'MERIT' differs by the following combination of characteristics as described in Table 1:

TABLE 1

| Characteristic | 'MERIT' | 'VALOR' (US PP 20,394) | 'PREMIER' (US PP 20,309) |
|---|---|---|---|
| 1. Color of mature fruit | Ranges from orange red to red | Ranges from red to dark red | Ranges from red to dark red |
| 2. Fruit size | Small | Medium | Medium |
| 3. Marketable yield (gm/plt) | 503 | 529 | 393 |

TABLE 1-continued

| Characteristic | 'MERIT' | 'VALOR' (US PP 20,394) | 'PREMIER' (US PP 20,309) |
|---|---|---|---|
| 4. Plant size | Ranges from medium to small | Medium | Medium |
| 5. Stolon anthocyanin intensity | Weak | Ranges from weak to medium | Ranges from weak to medium |
| 6. Stolon pubescence | Weak | Strong | Medium |
| 7. Color of upper surface | Medium green | Ranges from medium to dark green | Ranges from medium to dark green |
| 8. Interveinal leaf blistering | Ranges from medium to strong | Medium | Medium |
| 9. Foliage gloss | Medium | Medium | Ranges from medium to strong |
| 10. Serrations/leaf | 20.3 | 22.7 | 25.9 |
| 11. Petiole length (cm) | 14.2 | 17.4 | 15.5 |
| 12. Petiolule length (mm) | 11.9 | 17.8 | 11.8 |
| 13. Terminal leaf shape of base | Acute | Obtuse | Obtuse |
| 14. Fruiting truss length at maturity (cm) | 24.3 | 29.7 | 30.8 |
| 15. Fruiting truss pubescence | Medium | Ranges from medium to strong | Strong |

For identification a series of molecular markers have been determined for this new variety.

'MERIT' differs from its parents, 'PS-2880' and 'PS-4630' by the following combination of characteristics as described in Table 2.

TABLE 2

| Characteristic | 'MERIT' | 'PS-2880' (US PP 15,597) | 'PS-4630' |
|---|---|---|---|
| 1. Fruit size | Small | Medium | Large |
| 3. Plant size | Small | Medium to large | Medium to large |
| 4. Insertion of achenes | Level with surface | Above the surface | Level with surface |
| 5. Type of bearing | Everbearing | Everbearing | June bearing |

BRIEF DESCRIPTION OF THE PHOTOGRAPHS

The accompanying color photographs illustrate the overall appearance of typical specimens of the new strawberry variety 'MERIT', at various stages of development as true as it is reasonably possible with color reproductions of this type. Color in the photographs may differ slightly from the color value cited in the botanical descriptions which accurately describe the color of 'MERIT'. The depicted plant and plant parts of the new strawberry variety 'MERIT' are approximately 3 to 4 months old. The photographs were taken in Ventura County, California:

DETAILED BOTANICAL DESCRIPTION

Figure 1:
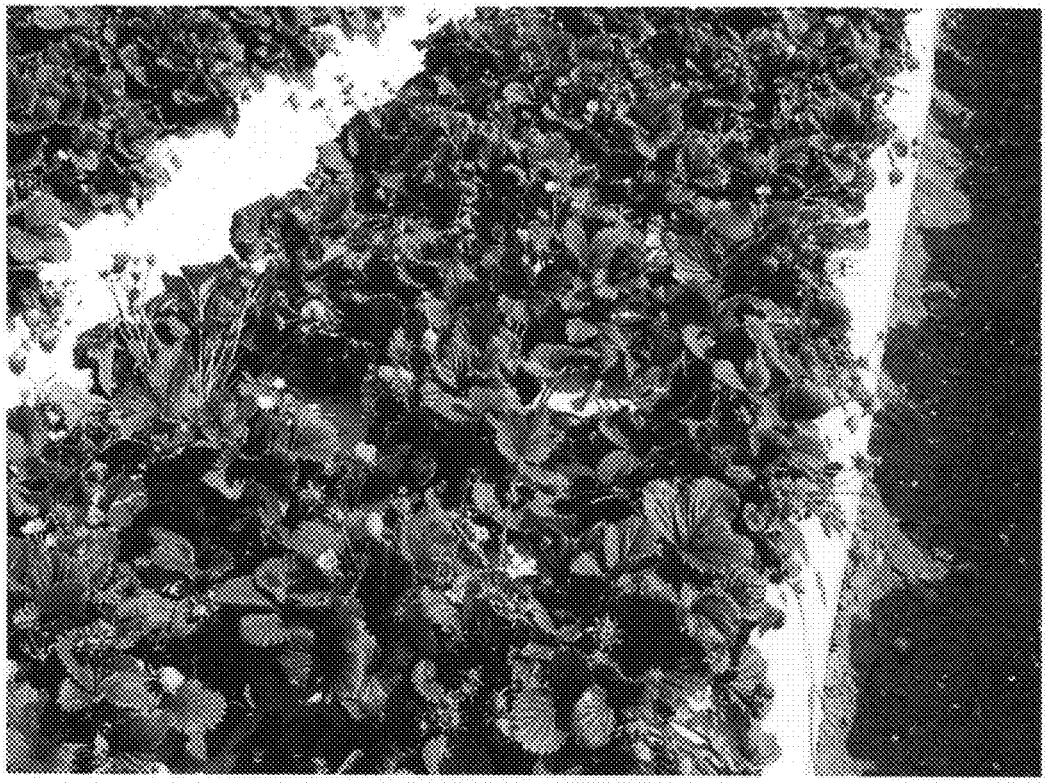
FIG. 1 shows typical fruiting field characteristics of 'MERIT' taken in the month of October 2009.
Figure 2:
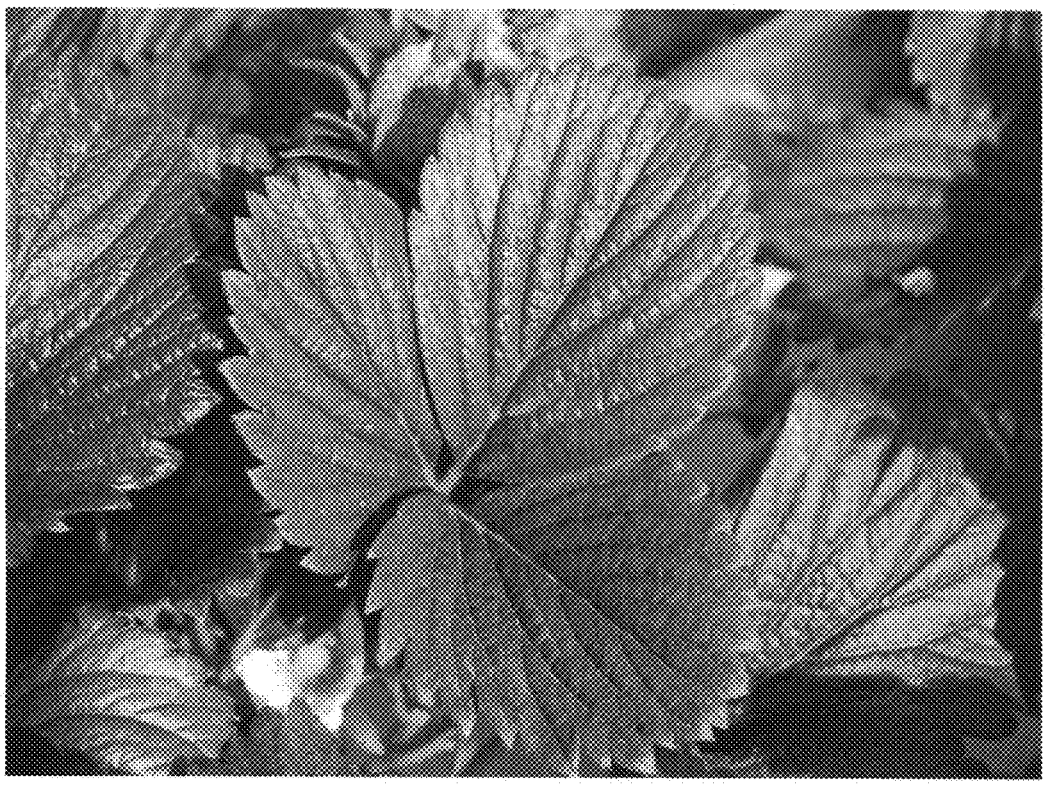
FIG. 2 shows a close-up view of a typical leaf structure of 'MERIT' taken in the month of October 2009.
Figure 3:
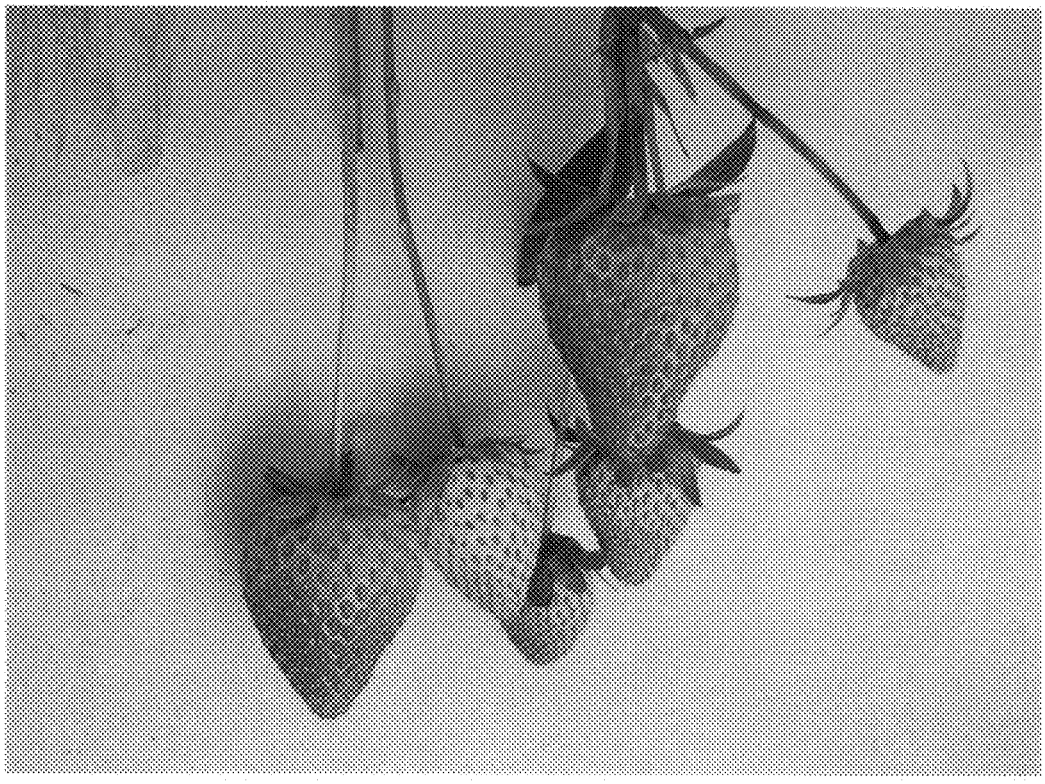
FIG. 3 shows typical mature and immature field fruit of 'MERIT' taken in the month of October 2009.
Figure 4:
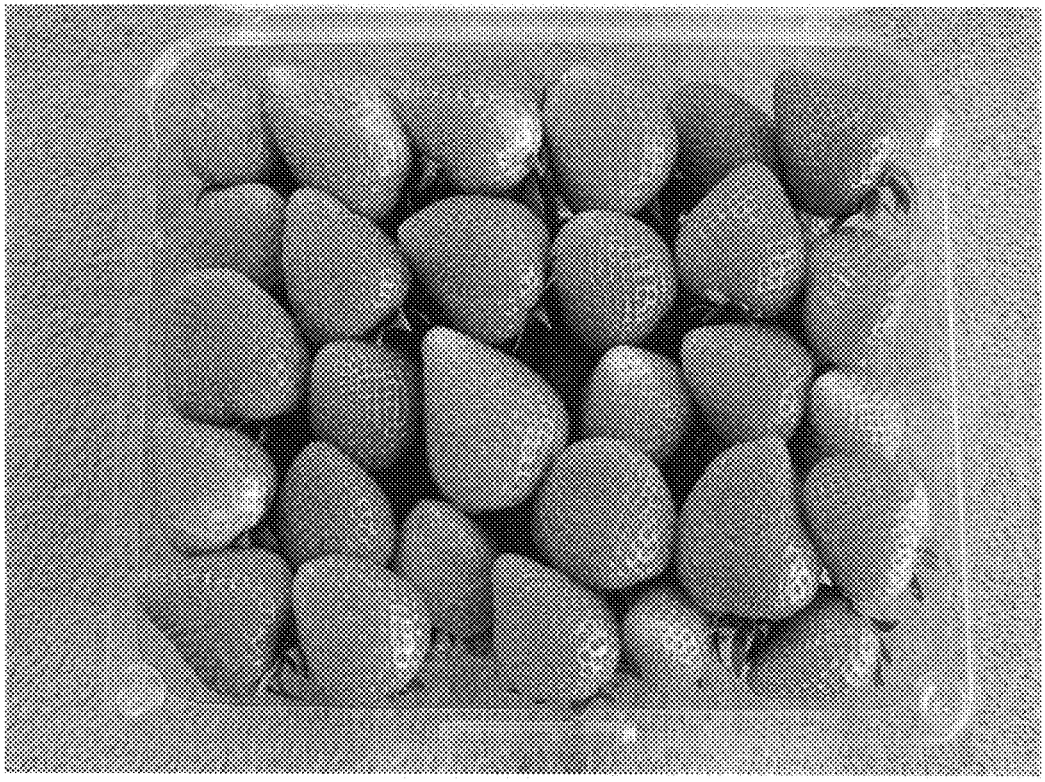
FIG. 4 shows a close-up view of mature fruit of 'MERIT' taken in the month of November 2009.
Figure 5:
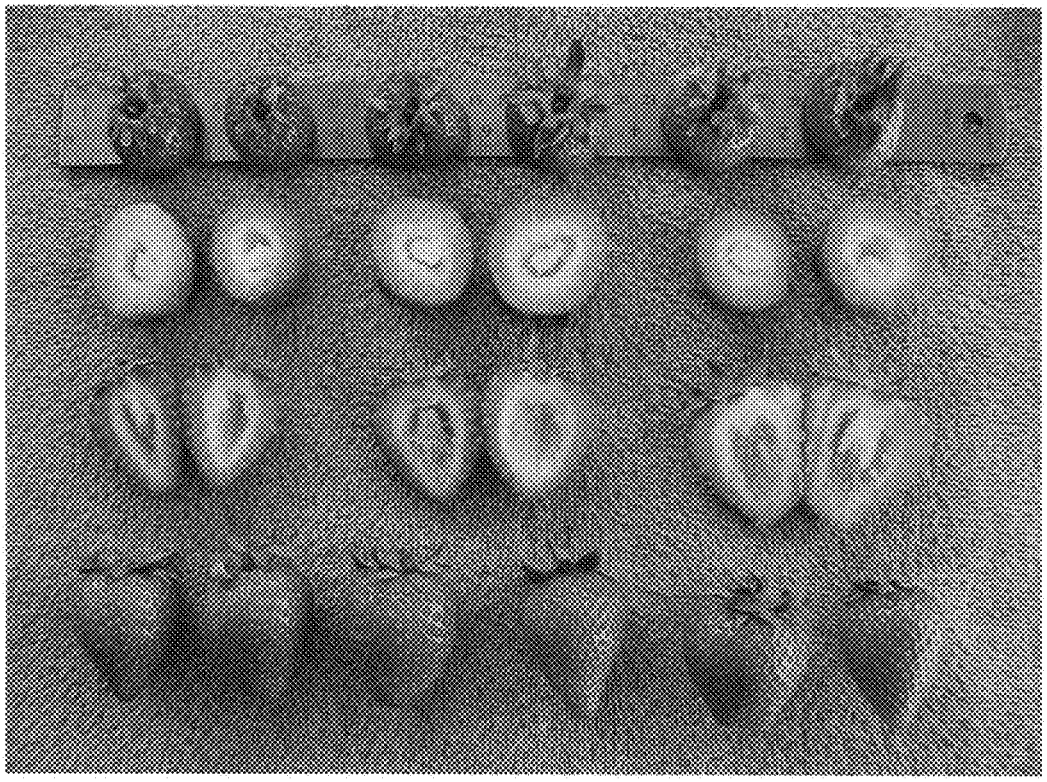
FIG. 5 shows typical internal and external mature fruit characteristics of 'MERIT' taken in the month of November 2009.

The new variety 'MERIT' has not been observed under all possible environmental conditions. The characteristics of the new variety 'MERIT' may vary in detail, depending upon variations in environmental factors, including weather (temperature, humidity and light intensity), day length, soil type and location. In addition, the characteristics of any parental variety or comparison variety included in Tables 1-9 of the present invention may vary in detail, depending upon variations in environmental factors, including weather (temperature, humidity and light intensity), day length, soil type and location.

The aforementioned photographs, together with the following description of the new variety 'MERIT', unless otherwise noted, are based on observations taken during the 2009 growing season in Ventura County, California. These measurements and ratings were taken from plants of 'MERIT' dug from a low-elevation nursery located in San Joaquin County, California during the month of January 2008 and planted approximately 6 months later in Ventura County, California. The approximate age of the observed plants is 3 to 4 months. Yield observations and fruit quality characteristics are averaged from four years of data collected from the 2006 through 2009 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following tables 3-9 describe fruit, plant, stolon, foliage, fruiting truss, flower and pest disease characteristics of the new strawberry 'MERIT' in comparison to the similar strawberry variety 'VALOR' and strawberry variety 'PREMIER'.

TABLE 3

FRUIT CHARACTERISTICS

| Characteristic | 'MERIT' | 'VALOR' (US PP 20,394) | 'PREMIER' (US PP 20,309) |
|---|---|---|---|
| Color of mature fruit | RHS 34B Ranges from orange red to red | RRHS 46A Ranges from red to dark red | RHS 46A Ranges from red to dark red |
| Color of internal flesh | RHS 34C Orange red | RHS 45A Ranges from medium to dark red | RHS 45A Ranges from medium to dark red |
| Fruit length (cm) | 3.8 | 4.0 | 4.2 |
| Fruit width (cm) | 3.3 | 3.6 | 3.5 |
| Fruit length/ width ratio | 1.14 Slightly longer than broad | 1.12 Slightly longer than broad | 1.22 Slightly longer than broad |
| Calyx diameter (cm) | 3.8 | 4.1 | 4.6 |
| Average fruit weight (gm) | 18.1 | 21.5 | 21.9 |
| Achene color, shaded side | RHS 160B Greyed yellow group | RHS 160A Greyed yellow group | RHS 160B Greyed yellow group |

TABLE 3-continued

| FRUIT CHARACTERISTICS | | | |
|---|---|---|---|
| Characteristic | 'MERIT' | 'VALOR' (US PP 20,394) | 'PREMIER' (US PP 20,309) |
| Achene color, sun exposed side | RHS 184B Greyed purple group | RHS 183A Greyed purple group | RHS 183A Greyed purple group |
| Achenes per berry | 324 | 331 | 286 |
| Achene weight (mg) | 0.50 | 0.50 | 0.60 |
| Marketable fruit yield (gm/plt) | 503 | 529 | 393 |
| Fruit Size | Small | Medium | Medium |
| Predominant fruit shape | Conical | Conical | Conical |
| Difference in shapes between primary and secondary fruit | Slight | Ranges from slight to moderate | None to very slight |
| Band without achenes | Absent or very narrow | Absent or very narrow | Absent or very narrow |
| Unevenness of fruit surface | Absent or very weak | Weak | Absent or very weak |
| Evenness of fruit color | Even | Even | Ranges from slightly uneven to even |
| Fruit glossiness | Ranges from medium to strong | Ranges from medium to strong | Ranges from medium to strong |
| Insertion of achenes | Level with surface | Ranges from level with to below the surface | Level with surface |
| Insertion of calyx | In the basin | In the basin | In the basin |
| Attitude of the calyx | Spreading | Spreading | Spreading |
| Size of calyx in relation to fruit diameter | Slightly larger | Slightly larger | Much larger |
| Adherence of calyx | Strong | Strong | Strong |
| Firmness of fruit skin | Medium | Strong | Medium |
| Firmness of fruit flesh | Firm | Firm | Medium |
| Keeping quality | Very good | Very good | Good |
| Distribution of red color of the flesh | Marginal and central | Marginal and central | Marginal and central |
| Hollow center expression | Moderate | Absent or very weak | Weak |
| Fruit flavor | Ranges from good to very good | Good | Good |
| Soluble solids (% brix) | 8.8 | 7.8 | 8.3 |
| Time of first flowering | Early | Medium | Medium |
| Time of first harvesting | Early | Medium | Medium |
| Harvest period | Late September to mid December | Late September to mid December | Late September to mid December |
| Type of bearing | Everbearing | Everbearing | Everbearing |

TABLE 4

| PLANT CHARACTERISTICS | | | |
|---|---|---|---|
| Characteristic | 'MERIT' | 'VALOR' (US PP 20,394) | 'PREMIER' (US PP 20,309) |
| Plant height (cm) | 24.1 | 25.9 | 25.6 |
| Plant spread (cm) | 29.0 | 31.6 | 33.5 |
| Plant size | Ranges from medium to small | Medium | Medium |
| Plant habit | Globose | Globose | Globose |
| Plant density | Medium | Medium | Medium |
| Plant vigor | Medium | Medium | Medium |

TABLE 5

| STOLON CHARACTERISTICS | | | |
|---|---|---|---|
| Characteristic | 'MERIT' | 'VALOR' (US PP 20,394) | 'PREMIER' (US PP 20,309) |
| Stolon color | RHS 145A Yellow green group | RHS 144A Yellow green group | RHS 145A Yellow green group |
| Stolon anthocyanin coloration | RHS 180D Greyed red group | RHS 180A Greyed red group | RHS 181 B Greyed red group |
| Stolon anthocyanin intensity | Weak | Ranges from weak to medium | Ranges from weak to medium |
| Average stolon number per plant from the fruiting field | 2.4 | 6.4 | 8.5 |
| Stolon diameter at bract (mm) | 3.1 | 3.3 | 3.6 |
| Stolon pubescence | Weak | Strong | Medium |
| Attitude of hairs | Upwards | Upwards | Upwards |

TABLE 6

| FOLIAGE CHARACTERISTICS | | | |
|---|---|---|---|
| Characteristic | 'MERIT' | 'VALOR' (US PP 20,394) | 'PREMIER' (US PP 20,309) |
| Foliage: | | | |
| Color of upper surface | RHS 137A Medium green | RHS N137B Medium to dark green | RHS N137B Medium to dark green |
| Color of underside | RHS 147C Yellow green group | RHS 147C Yellow green group | RHS 147C Yellow green group |
| Shape in cross section | Slightly concave to flat | Slightly concave to flat | Slightly concave |
| Interveinal blistering | Ranges from medium to strong | Medium | Medium |
| Leaf glossiness | Medium | Medium | Ranges from medium to strong |
| Number of leaflets | Three | Three | Three |
| Terminal Leaflet: | | | |
| Length (cm) | 8.9 | 8.6 | 9.6 |
| Width (cm) | 7.6 | 8.7 | 8.6 |
| Length/width ratio | 1.18 Longer than broad | 0.99 As long as broad | 1.11 Longer than broad |

TABLE 6-continued

| FOLIAGE CHARACTERISTICS | | | |
|---|---|---|---|
| Characteristic | 'MERIT' | 'VALOR' (US PP 20,394) | 'PREMIER' (US PP 20,309) |
| Serrations/leaf | 20.3 | 22.7 | 25.9 |
| Leaf size | Ranges from medium to small | Medium | Medium |
| Shape of base | Acute | Obtuse | Obtuse |
| Shape of teeth | Obtuse | Obtuse | Obtuse |
| Petiole: | | | |
| Petiole Color | RHS 144A Yellow green group | RHS 144A Yellow green group | RHS 144A Yellow green group |
| Petiole length (cm) | 14.2 | 17.4 | 15.5 |
| Petiole diameter (mm) | 3.4 | 4.2 | 4.3 |
| Petiolule color | RHS 144A Yellow green group | RHS 144A Yellow green group | RHS 144A Yellow green group |
| Petiolule length (mm) | 11.9 | 17.8 | 11.8 |
| Petiole pubescence | Moderate | Sparce | Sparce |
| Attitude of hairs | Strongly outward | Strongly outward | Strongly outward |
| Stipule: | | | |
| Color | RHS 146A Yellow green group | RHS 146A Yellow green group | RHS 146B Yellow green group |
| Anthocyanin coloration | RHS 63A Red purple group | RHS 61A Red purple group | RHS 61A Red purple group |
| Anthocyanin intensity | Weak | Weak | Medium |
| Length (mm) | 22.2 | 21.3 | 24.8 |
| Width (mm) | 8.6 | 10.4 | 11.3 |

TABLE 7

| FRUITING TRUSS CHARACTERISTICS | | | |
|---|---|---|---|
| Characteristic | 'MERIT' | 'VALOR' (US PP 20,394) | 'PREMIER' (US PP 20,309) |
| Anthocyanin coloration | RHS 181D Greyed red group | RHS 181C Greyed red group | RHS 181B Greyed red group |
| Anthocyanin intensity | Absent or very weak | Absent or very weak | Medium |
| Length at maturity (cm) | 24.3 | 29.7 | 30.8 |
| Position relative to foliage | Above the foliage | Level with the foliage | Ranges from level with to beneath the foliage |
| Pubescence | Medium | Ranges from medium to strong | Strong |
| Attitude at first pick | Prostrate | Prostrate | Prostrate |

TABLE 8

| FLOWER CHARACTERISTICS | | | |
|---|---|---|---|
| Characteristic | 'MERIT' | 'VALOR' (US PP 20,394) | 'PREMIER' (US PP 20,309) |
| Petal color | RHS NN155C White | RHS NN155C White | RHS NN155C White |
| Sepal color | RHS 137A Green group | RHS 137A Green group | RHS 137A Green group |
| Corolla diameter (mm) | 31.0 | 30.1 | 35.3 |
| Calyx diameter (mm) | 29.8 | 31.2 | 33.9 |
| Petal length (mm) | 11.7 | 11.3 | 13.4 |
| Petal width (mm) | 12.0 | 11.1 | 12.7 |
| Petal length/ width ratio | 0.98 | 1.02 | 1.05 |
| Petals/flower | 6.2 | 5.7 | 5.8 |
| Sepal length (mm) | 11.0 | 10.5 | 12.3 |
| Sepal width (mm) | 3.2 | 4.7 | 5.8 |
| Sepal length/ width ratio | 3.41 | 2.23 | 2.11 |
| Sepals/flower | 11.8 | 11.4 | 11.6 |
| Size of calyx relative to corolla | Ranges from same size to smaller | Larger | Larger |
| Size of inner calyx relative to outer calyx | Smaller | Smaller | Smaller |
| Relative position of petals | Overlapping | Ranges from touching to overlapping | Overlapping |

TABLE 9

| PEST AND DISEASE REACTIONS | | | |
|---|---|---|---|
| Characteristic | 'MERIT' | 'VALOR' (US PP 20,394) | 'PREMIER' (US PP 20,309) |
| Two spotted spider mite | Moderately susceptible | Moderately susceptible | Moderately susceptible |
| Flower thrips | Moderately susceptible | Moderately susceptible | Moderately susceptible |
| Powdery mildew | Moderately susceptible | Susceptible | Susceptible |
| Botrytis fruit rot | Moderately susceptible | Moderately susceptible | Moderately susceptible |
| Angular leaf spot | Moderately resistant | Moderately susceptible | Susceptible |

We claim:

1. A new and distinct variety of *Fragaria ananassa* named 'MERIT', as herein described and illustrated by the characteristics set forth above.

* * * * *